United States Patent [19]

Uhle et al.

[11] 4,369,648
[45] Jan. 25, 1983

[54] TESTING METHOD FOR DETERMINING THE MAGNETIC PROPERTIES OF FERROMAGNETIC POWDERS

[75] Inventors: Karlheinz Uhle, Brühl; Horst Krämer, Hürth-Hermülheim, both of Fed. Rep. of Germany

[73] Assignee: Hoechst Aktiengesellschaft, Fed. Rep. of Germany

[21] Appl. No.: 261,744

[22] Filed: May 8, 1981

[30] Foreign Application Priority Data

May 16, 1980 [DE] Fed. Rep. of Germany ....... 3018640

[51] Int. Cl.$^3$ ........................................... G01N 15/04
[52] U.S. Cl. ....................................... 73/61.4; 209/8; 356/442
[58] Field of Search ................. 73/61.4; 356/441, 442; 209/8, 39

[56] References Cited

FOREIGN PATENT DOCUMENTS 488118 1/1976 U.S.S.R. ............................... 73/61.4
623140 9/1978 U.S.S.R. ............................... 73/61.4

Primary Examiner—Edward R. Kazenske
Assistant Examiner—Joseph W. Roskos
Attorney, Agent, or Firm—Connolly and Hutz

[57] ABSTRACT

The invention relates to a method permitting ferromagnetic powders to be readily tested for their qualification for use in heavy medium suspensions for the float-sink dressing of minerals. To this end, the invention provides (a) for ferromagnetic powder particles with a size within the range 63 to 100$\mu$ to be admixed with a quantity of a glycerol/water mixture necessary to obtain a heavy medium suspension having a specific density within the range 1.45 to 1.55 g/cm$^3$;

(b) for the heavy medium suspension to be demagnetized in a cyclicly decreasing alternating field at maximum field strengths within the range 1200 to 1600 amperes/cm and for its relative sedimentation velocity to be determined by means of a sedimentometer;

(c) for the demagnetized heavy medium suspension to be magnetized in a magnetic steady field at field strengths within the range 700 to 900 amperes/cm and for its relative sedimentation velocity to be determined by means of a sedimentometer; and for (d) the magnetized heavy medium suspension to be demagnetized in a cyclicly decreasing alternating field at maximum field strengths within the range 1200 to 1600 amperes/cm and for its relative sedimentation velocity to be determined by means of a sedimentometer.

Ferromagnetic powder is fully serviceable for use in heavy medium suspensions in the event of the relative sedimentation velocity determined in step (b) being smaller than 0.25 cm/second, that determined in step (c) being greater than 2.5 cm per second and that determined in step (d) being smaller than 0.4 cm/second.

2 Claims, 1 Drawing Figure

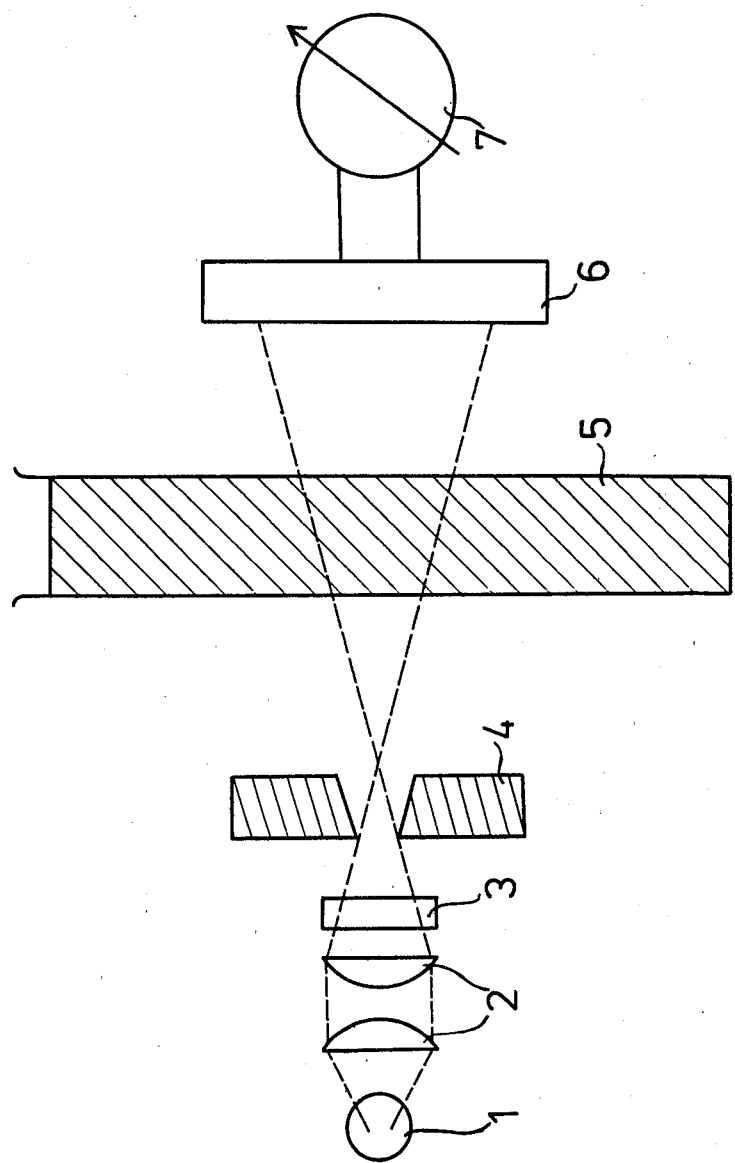

TESTING METHOD FOR DETERMINING THE MAGNETIC PROPERTIES OF FERROMAGNETIC POWDERS

The present invention provides a testing method for determining the magnetic properties of ferromagnetic powders for use in heavy medium suspensions for the float-sink dressing of minerals.

Float-sink dressing is a process which is customarily used for separating minerals of different density from each other with the use of an aqueous suspension of a heavy medium, i.e. with the use of a so-called heavy medium suspension with a specific density which lies between the densities of the respective minerals which are to be separated from each other. As a result, upon the introduction of the mixture of minerals into the heavy medium suspension, it is possible for mixture constituents of lower density to float thereon, and for mixture constituents of higher density to sink down and settle therein. Needless to say portions of heavy medium suspension adhere to the floating and settled materials. For recovery, the materials are separated from one another and subjected to treatment with a water jet, the adhering heavy medium being then obtained in the form of a dilute suspension. The small particle size makes it impossible for the heavy medium to be separated, e.g. by filtration from such dilute suspension. This is the reason why ferromagnetic powders are preferentially used as heavy media as these can be recovered from a dilute suspension by magnetic separation and can additionally be freed from unmagnetic contaminants. Magnetite has more particularly been used for making heavy medium suspensions of relatively low specific density, and ferrosilicon with 8 to 25% Si therein has been used for making heavy medium suspensions of higher specific density, the heavy medium, which is incidentally made by a spray or grinding process, being employed in the form of particles with a size within the range about 0.001 to 0.4 mm. Magnetically separated heavy medium is invariably magnetized, i.e. constitutes powder which is unable to produce a stable suspension. In other words, any heavy medium which is so recovered has to be demagnetized for re-use in the preparation of fresh heavy medium suspensions. It has been described that any recovered heavy medium can be demagnetized by subjecting it to treatment at temperatures higher than its Curie point, or less expensively, by demgnetization in an alternating field. Depending on the available production facility, quality and quantity of the feed material, it is possible to produce pulverulent heavy media with more or less good magnetic properties, which naturally influence their demagnetizability in the alternating field. Especially in those cases in which the heavy medium, e.g. ferrosilicon, has further corrosion-improving materials, e.g. carbon together with phosphorus, copper, aluminium or similar materials admixed with it, (cf. German Patent Nos. 972,687 and 2,222,657) the resulting multimaterial system cannot be said to have well-defined magnetic properties.

It is therefore the object of the present invention to provide a method permitting ferromagnetic powders to be readily tested for their qualification for use in heavy medium suspensions for the float-sink dressing of minerals, which comprises:

(a) admixing ferromagnetic powder particles with a size within the range 63 to 100$\mu$ with a quantity of a glycerol/water mixture necessary to obtain a heavy medium suspension having a specific density within the range 1.45 to 1.55 g/cm$^3$;

(b) demagnetizing the heavy medium suspension in a cyclicly decreasing alternating field at maximum field strengths within the range 1200 to 1600 amperes/cm and determining its relative sedimentation velocity by means of a sedimentometer;

(c) magnetizing the demagnetized heavy medium suspension in a magnetic steady field at field strengths within the range 700 to 900 amperes/cm and determining its relative sedimentation velocity by means of a sedimentometer; and (d) demagnetizing the magnetized heavy medium suspension in a cyclicly decreasing alternating field at maximum field strengths within the range 1200 to 1600 amperes/cm and determining its relative sedimentation velocity by means of a sedimentometer;

the ferromagnetic powder being fully serviceable for use in heavy medium suspensions in the event of the relative sedimentation velocity determined in step (b) being smaller than 0.25 cm/second, that determined in step (c) being greater than 2.5 cm per second and that determined in step (d) being smaller than 0.4 cm/second.

A preferred feature of the invention provides for the glycerol/water-mixture to contain glycerol and water in a ratio by weight of (0.9 to 1.1):1.

It is also preferable for the ferromagnetic powder to be admixed with the glycerol/water-mixture inside a glass cylinder with a length of about 18 to 20 cm, an outer diameter of 18 to 20 cm and a wall thickness of 1.0 to 1.5 mm, for the individual magnetizing and demagnetizing operations, and the respective relative sedimentation velocities to be effected therein.

Use is made of quantitatively small specimens in the testing method of this invention which permits ferromagnetic powder for use in heavy medium suspensions to be rapidly tested as to whether, on the one hand, it is magnetizable enough to ensure reliable magnetic separation from an aqueous phase and as to whether, on the other hand, it is magnetically soft enough to ensure satisfactory demagnetization.

The sedimentometer used in the testing method of this invention is shown diagrammatically in the accompanying drawing.

With reference thereto:

A collector system 2 formed of a plurality of lenses is exposed to the light of a low-voltage lamp, which is used as a light source 1. The light ray coming from the collector system 2 is passed through a heat-absorbing filter 3 and a slit-shaped shutter 4 and directed to impinge upon a glass cylinder 5 having heavy medium suspension placed in it. The light ray portion penetrating through the glass cylinder 5 impinges upon a photoelectric cell 6 which is electrically connected to a measuring instrument 7.

Depending on the sedimentation velocity determined for the powder in the heavy medium suspension, the measuring instrument 7 commences deflecting when the last powder particles which are largest in diameter just have dropped past it.

The sedimentation velocity is determined in accordance with the testing method of this invention on the evidence of the spacing between the slit-shaped shutter 4 and the level of heavy medium suspension in the glass cylinder 5 and the period which elapses from the insertion, into the sedimentometer, of the glass cylinder 5 just filled with freshly agitated or shaken heavy medium suspension, until response of the measuring instrument 7 by a defined deflection. The defined deflection is 10% of that which is produced by the measuring instrument 7 in the event of the glass cylinder 5 being filled with a glycerol/water-mixture free from solid matter and with the glycerol/water ratio by weight specified hereinabove.

EXAMPLE 1:

13 ml of a glycerol/water-mixture (ratio by weight=1:1) was placed in a glass cylinder with a length of 18 cm and an outer diameter of 18 cm, and the glass cylinder was placed in the sedimentometer. After one second, the measuring instrument indicated a photoelectric current of 3 µA, which remained unchanged.

The glass cylinder was taken from the sedimentometer and filled with 10 g pulverulent ferrosilicon which contained 12.5 weight % silicon and 1 weight % of phosphorus and had a particle size of 63 to 100 µ, so as to produce a heavy medium suspension therein. The suspension was shaken and then demagnetized in a cyclicly decreasing alternating field at a maximum field strength of 1200 amperes/cm. The suspension was shaken once again and placed in the sedimentometer. After 40 seconds, the photoelectric current was found to be 0.3 µA. Calculation based thereon and the 8 cm spacing between the suspension level and slit-shaped shutter indicated a relative sedimentation velocity of 0.20 cm/second. The heavy medium suspension was shaken once again and then magnetized in a magnetic steady field of 700 amperes/cm and the shaken suspension was placed again in the sedimentometer. After 2.6 seconds, the photoelectric current was found to be 0.3 µA. Calculation based thereon and the 8 cm spacing between the suspension level and slit-shaped shutter indicated a relative sedimentation velocity of 3.1 cm/second. The suspension was shaken again and then demagnetized in a cyclicly decreasing alternating field at a maximum field strength of 1200 amperes/cm. The shaken suspension was placed in the sedimentometer, of which the measuring instrument indicated a photo-electric current of 0.3 µA, after 28.6 seconds. Calculation based thereon and the 8 cm spacing between the suspension level and slit-shaped shutter indicated a relative sedimentation velocity of 0.28 cm/second.

EXAMPLES 2 TO 8:

The procedure was the same as in Example 1 but ferrosilicon powder with varying proportions of silicon and phosphorus was used.

The proportions of silicon and phosphorus contained in the various ferrosilicon powders used in Examples 1 to 8 and their relative sedimentation velocities (I: after first demagnetizing operation; II: after remagnetization; III: after second demagnetizing operation) are indicated in the following Table.

| Ex. No. | Wgt % Si | Wgt % P | Relative sedimentation velocity cm/s | | |
|---|---|---|---|---|---|
| | | | I | II | III |
| 1 | 12.5 | 1.0 | 0.20 | 3.1 | 0.28 |

-continued

| Ex. No. | Wgt % Si | Wgt % P | Relative sedimentation velocity cm/s | | |
|---|---|---|---|---|---|
| | | | I | II | III |
| 2 | 11.9 | 1.5 | 0.22 | 2.8 | 0.26 |
| 3 | 15.0 | 2.0 | 0.23 | 2.6 | 0.27 |
| 4 | 14.5 | 2.7 | 0.24 | 2.6 | 0.53 |
| 5 | 14.9 | 3.0 | 0.24 | 2.6 | 0.80 |
| 6 | 15.6 | 2.5 | 0.23 | 2.8 | 1.6 |
| 7 | 13.1 | 4.2 | 0.28 | 3.2 | 0.90 |
| 8 | 12.0 | 6.1 | 0.30 | 3.0 | 1.3 |

The ferrosilicon powders used in Examples 1 to 3 had the following relative sedimentation velocities:
I smaller than 0.25 cm/second
II higher than 2.5 cm/second
III smaller than 0.4 cm/second.
They were fully serviceable for use in heavy medium suspension for the float-sink dressing of minerals.

The ferrosilicon powders used in Examples 4 and 5 had relative sedimentation velocities III varying between 0.4 and 1 cm/second. These are powders which are liable to give rise to difficulties in the float-sink dressing process.

The ferrosilicon powders used in Examples 6 to 8 had relative sedimentation velocities of which practically all were found to differ from those determined for the ferrosilicon powder used in Examples 1 to 3. These are powders which are unsuitable for use in heavy medium suspensions for float-sink dressing.

We claim:
1. A method permitting ferromagnetic powders to be readily tested for their qualification for use in heavy medium suspensions for the float-sink dressing of minerals, which comprises:
(a) admixing ferromagnetic powder particles with a size within the range 63 to 100µ with a quantity of a glycerol/water mixture necessary to obtain a heavy medium suspension having a specific density within the range 1.45 to 1.55 g/cm³; and subjecting the suspension to the following three magnetic operations comprising:
(b) demagnetizing the heavy medium suspension in a cyclicly decreasing alternating field at maximum field strengths within the range 1200 to 1600 amperes/cm and determining its relative sedimentation velocity by means of a sedimentometer;
(c) magnetizing the demagnetized heavy medium suspension in a magnetic steady field at field strengths within the range 700 to 900 amperes/cm and determining its relative sedimentation velocity by means of a sedimentometer; and
(d) demagnetizing the magnetized heavy medium suspension in a cyclicly decreasing alternating field at maximum field strengths within the range 1200 to 1600 amperes/cm and determining its relative sedimentation velocity by means of a sedimentometer; the ferromagnetic powder being fully serviceable for use in heavy medium suspensions in the event of the relative sedimentation velocity determined in step (b) being smaller than 0.25 cm/second, that determined in step (c) being greater than 2.5 cm per second and that determined in step (d) being smaller than 0.4 cm/second.
2. The testing method as claimed in claim 1, wherein the glycerol/water-mixture contains glycerol and water in a ratio by weight of (0.9 to 1.1):1.

* * * * *